(12) United States Patent
Delanoy et al.

(10) Patent No.: US 12,188,931 B2
(45) Date of Patent: Jan. 7, 2025

(54) BORRELIA IMMUNOASSAYS AND MATERIALS THEREFOR

(71) Applicant: BIO-RAD LABORATORIES, INC., Hercules, CA (US)

(72) Inventors: Michelle Delanoy, Danville, CA (US); John Flanagan, Walnut Creek, CA (US); Audrey Arjomandi, San Francisco, CA (US); Ravi Kaul, Davis, CA (US); Steven R. Binder, Hercules, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 68 days.

(21) Appl. No.: 17/562,055

(22) Filed: Dec. 27, 2021

(65) Prior Publication Data
US 2022/0137047 A1    May 5, 2022

Related U.S. Application Data

(62) Division of application No. 15/766,525, filed as application No. PCT/US2016/055618 on Oct. 6, 2016, now Pat. No. 11,209,431.

(60) Provisional application No. 62/237,846, filed on Oct. 6, 2015.

(51) Int. Cl.
*C07K 14/20* (2006.01)
*A61K 39/02* (2006.01)
*G01N 33/569* (2006.01)

(52) U.S. Cl.
CPC .... *G01N 33/56911* (2013.01); *A61K 39/0225* (2013.01); *C07K 14/20* (2013.01); *G01N 2333/20* (2013.01)

(58) Field of Classification Search
None
See application file for complete search history.

(56) References Cited

U.S. PATENT DOCUMENTS

| | | | |
|---|---|---|---|
| 6,475,492 | B1 | 11/2002 | Philipp et al. |
| 7,008,625 | B2 | 3/2006 | Dattwyler et al. |
| 7,582,304 | B2 | 9/2009 | Dattwyler et al. |
| 7,887,815 | B2 | 2/2011 | Dattwyler et al. |
| 8,758,772 | B2 | 6/2014 | Mehra et al. |
| 8,778,352 | B2 | 7/2014 | Marconi et al. |
| 8,808,705 | B2 | 8/2014 | Marconi et al. |
| 11,209,431 | B2 | 12/2021 | Delanoy et al. |
| 2009/0162875 | A1 | 6/2009 | Dattwyler et al. |
| 2013/0129764 | A1 | 5/2013 | Atkinson et al. |
| 2015/0017666 | A1 | 1/2015 | Dattwyler et al. |
| 2015/0064208 | A1 | 3/2015 | Marconi et al. |
| 2018/0149648 | A1 | 5/2018 | Lukinova et al. |

FOREIGN PATENT DOCUMENTS

| | | |
|---|---|---|
| CA | 2 708 753 | 12/2011 |
| WO | WO 95/14781 | 6/1995 |
| WO | WO 00/78800 | 12/2000 |
| WO | WO 00/78966 | 12/2000 |
| WO | WO 2009/033163 | 3/2009 |
| WO | WO 2013/116668 | 8/2013 |
| WO | WO 2014/028726 | 2/2014 |
| WO | WO 2015/085323 | 6/2015 |
| WO | WO 2016/049148 | 3/2016 |
| WO | WO 2016/057562 | 4/2016 |
| WO | WO 2017/031216 | 2/2017 |

OTHER PUBLICATIONS

Written Opinion in International Application No. PCT/US2016/055618, Mar. 30, 2017, pp. 1-8.
Lahey, L. J. et al. "Development of a Multiantigen Panel for Improved Detection of *Borrelia burgdorferi* Infection in Early Lyme Disease" *Journal of Clinical Microbiology*, Dec. 2015, pp. 3834-3841, vol. 53, No. 12.
Burbelo, P. D. et al. "Rapid, Simple, Quantitative, and Highly Sensitive Antibody Detection for Lyme Disease" *Clinical and Vaccine Immunology*, Jun. 2010, pp. 904-909, vol. 17, No. 6.
Glatz, M. et al. "Immunoblot Analysis of the Seroreactivity to Recombinant *Borrelia burgdorferi* sensu lato Antigens, Including VlsE, in the Long-Term Course of Treated Patients with Erythema Migrans" *Dermatology*, 2008, pp. 93-103, vol. 216.
Polyak, S. J. et al. "The P58 Cellular Inhibitor Complexes with the Interferon-induced, Double-stranded RNA-dependent Protein Kinase, PKR, to Regulate Its Autophosphorylation and Activity" *J. Biol. Chem.*, Jan. 19, 1996, pp. 1702-1707, vol. 271, No. 3.
Wodecka, B. "flaB Gene as a Molecular Marker for Distinct Identification of *Borrelia* Species in Environmental Samples by the PCR-Restriction Fragment Length Polymorphism Method" *Appl. Environ. Microbial.*, Oct. 2011, pp. 7088-7092, vol. 77, No. 19.
Wilske, B. et al. "Immunological and Molecular Polymorphisms of OspC, an Immunodominant Major Outer Surface Protein of *Borrelia burgdorferi*" *Infection and Immunity*, May 1993, pp. 2182-2191, vol. 61, No. 5.

(Continued)

*Primary Examiner* — S. Devi
(74) *Attorney, Agent, or Firm* — SALIWANCHIK, LLOYD & EISENSCHENK

(57) ABSTRACT

The present invention relates to an immunoassay for the detection of *Borrelia* specific IgG, IgM and IgG/IgM antibodies in biological samples suspected of Lyme infection. The immunoassay can be performed via a standard immunoassay format or on an automated platform. In various embodiments, the immunoassay uses one or more *Borrelia* specific chimeric peptides VlsE-FlaB (designated pFlaB-mV), VlsE-ErpP (designated pErp59-mV), VlsE-P35 (designated pP35-mV) alone or in combination with one or more outer surface protein C (Osp C) types B or I, p58 and DbpA. Other aspects of the invention provide antigen/substrate combinations and compositions comprising combinations of the disclosed peptides and/or proteins for use in the immunoassays described herein.

11 Claims, 2 Drawing Sheets
Specification includes a Sequence Listing.

(56) References Cited

OTHER PUBLICATIONS

Wikipedia publication—Borrelia, pp. 1-10, 2020.
Colman, P. M. "Effects of amino acid sequence changes on antibody-antigen interactions" *Research Immunol.*, 1994, pp. 33-36, vol. 145.
Greenspan, N. S. et al. "Defining epitopes: It's not as easy as it seems" *Nature Biotechnology*, Oct. 1999, pp. 936-937, vol. 17.

BORRELIA IMMUNOASSAYS AND MATERIALS THEREFOR

CROSS-REFERENCE TO RELATED APPLICATIONS

This application is a divisional of U.S. Ser. No. 15/766,525, filed Apr. 6, 2018, now U.S. Pat. No. 11,209,431, which is the U.S. national stage application of International Patent Application No. PCT/US2016/055618, filed Oct. 6, 2016, which claims the benefit of U.S. Provisional Application Ser. No. 62/237,846, filed Oct. 6, 2015, the disclosures of which are hereby incorporated by reference in their entirety, including all figures, tables and amino acid or nucleic acid sequences.

REFERENCE TO SEQUENCE LISTING

The Sequence Listing for this application is labeled "Seq-List.txt" which was created on Apr. 4, 2018 and is 12 KB. The entire content of the sequence listing is incorporated herein by reference in its entirety.

BACKGROUND OF THE INVENTION

*Borrelia burgdorferi*, a spirochete, is the causative agent of Lyme disease. It is a vector borne pathogen, transmitted by ticks of the *Ixodes scapularis* and *Ixodes pacificus*. Infection with *B. burgdorferi* is the most common tick-borne infectious disease in North America and Europe. In endemic areas, between 30 and 90% of *Ixodes* ticks are infected with *Borrelia* organism. Lyme disease is a progressive multi-system disorder that can affect the skin, central nervous system, peripheral nerves, the heart and the joints, with nerve and joint involvement being the most common (1).

The clinical course of disease can be divided into three stages: early localized, early disseminated and late disseminated. Beyond the presence of an erythema migrans (EM), the individual signs and symptoms of disease are not sufficient to make a diagnosis (2). In Europe the dissemination of endemic *B. garinii* and *B. afzelii* occurs through the peripheral nerves while in USA the dissemination is predominantly through blood. European presentations are confounded by a lower incidence of recognized erythema migrans. The pathogenesis to a chronic state of nerve involvement, termed neuroborreliosis, is unclear, but may be due to a direct effect of the spirochetes at the site of infection, the host response to *B. burgdorferi*, or the host response to tissue antigens that may mimic those of *Borrelia burgdorferi* (3). There are very few reports showing the isolation of spirochetes from synovial fluid and nerve biopsy cultures especially as the disease progresses.

A natural antibody response to the pathogen develops over the early weeks of infection that persists over a longer period of time. Serological assays measuring antibody responses and profiles have been mainstay of laboratory confirmation. In 1995, the Centers for Disease Control and Prevention (CDC) recommended a two tier serological testing algorithm that utilizes a first-tier enzyme immunoassay (EIA) followed by second-tier Western immunoblot (WB) assay to standardize the laboratory evidence of exposure to *B. burgdorferi* (4, 5). A similar strategy was established in Europe as well (6). The suboptimal sensitivity of two tiered testing algorithm in early Lyme disease has led to confusion and misunderstanding of the value of testing. However, in late-stage Lyme arthritis or Lyme neuroborreliosis, the two tier sensitivity is much higher, ranging from 97%-100% (7, 8). The present invention relates to the development of a novel test for the detection of *Borrelia* antibodies in patient samples suspected of having Lyme disease and provides a solution to the problem of detection of Lyme disease in acutely infected subjects.

BRIEF SUMMARY OF THE INVENTION

The present invention relates to the development of a novel immunoassay for the detection of *Borrelia* antibodies in patient samples suspected of Lyme disease. The immunoassay can be performed via a standard immunoassay format or on an automated platform. In various embodiments, the immunoassay uses one or more *Borrelia* specific chimeric peptides VlsE-FlaB (designated pFlaB-mV), VlsE-ErpP (designated pErp59-mV), VlsE-P35 (designated pP35-mV) alone or in combination with one or more outer surface protein C (Osp C) proteins (e.g., Osp C types B or I), p58 and DbpA. Other embodiments provide for immunoassays in which single peptide or protein selected from pFlaB-mV, pErp59-mV, pP35-mV), p58, Osp C proteins (e.g., Osp C type B or type I), and DbpA is immobilized on a substrate and used for the detection of antibodies in biological samples obtained from subjects. Yet other embodiments provide immunoassays utilizing multivalent antigens composed of two or more of the aforementioned *Borrelia* specific peptides and proteins selected from pFlaB-mV, pErp59-mV and pP35-mV, p58, Osp C (e.g., Osp C type B or type I) and DbpA. In various embodiments, the immunoassays can use labeled antibodies (e.g., IgG-PE and/or IgM-PE reporters that bind to IgG and/or IgM antibodies in the tested biological sample) to detect and/or quantify *Borrelia*-specific antibodies in the biological sample (e.g., a serum or cerebro-spinal fluid (CSF) sample from a subject). Other aspects of the invention provide antigen/substrate combinations for use in the immunoassays described herein.

DETAILED DISCLOSURE OF THE INVENTION

Figure 1:
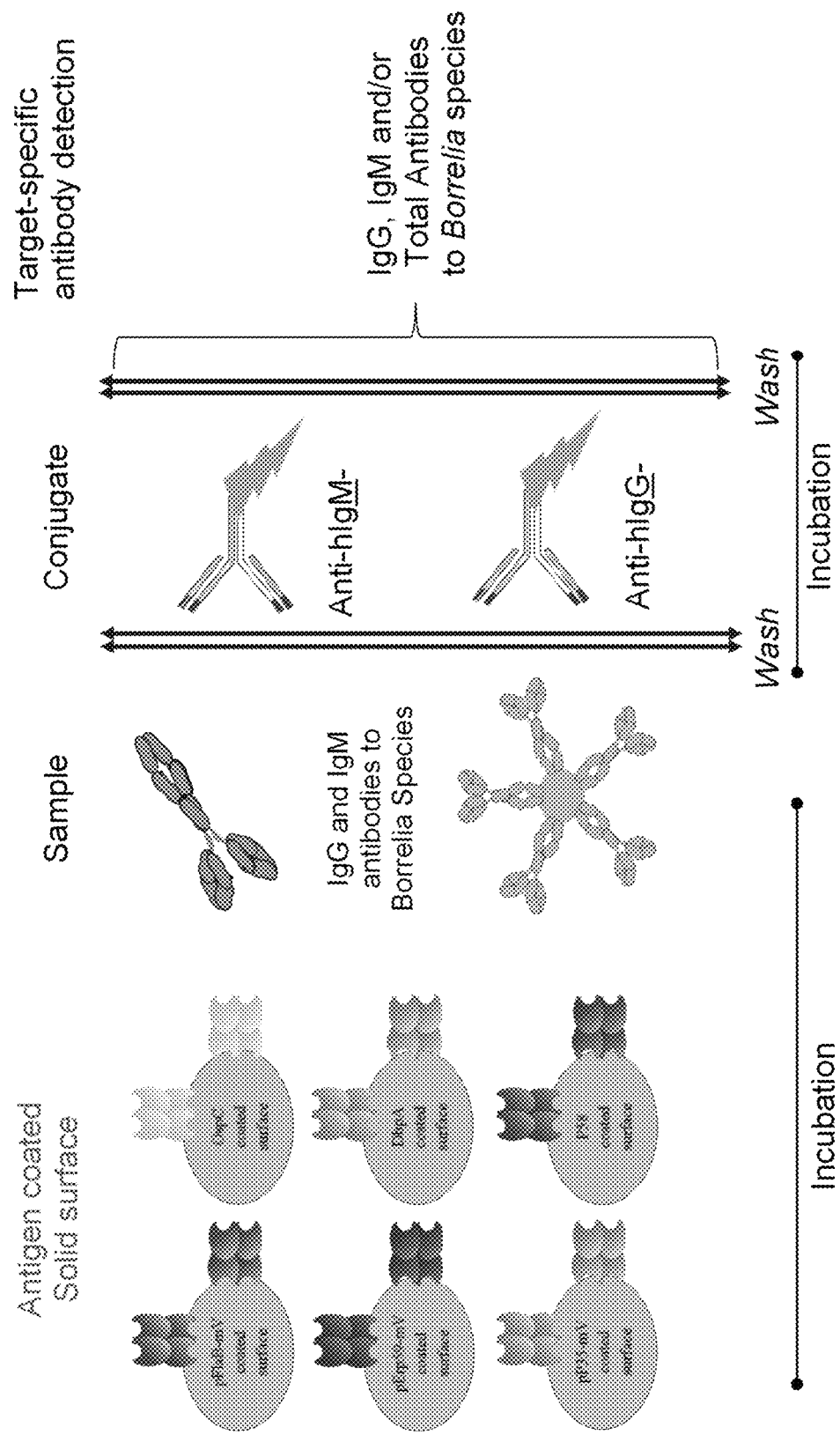
FIGS. 1-3 show a schematic illustration of a combination (multiplex) assay format for the detection of Lyme total (IgG and IgM) antibodies (FIG. 1), Lyme IgG antibodies (FIG. 2) and Lyme IgM antibodies (FIG. 3) on the BIOPLEX 2200 platform.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N.Y. 1989). The present disclosure may refer to items such as labels, solid supports, beads, analytes, etc. according to number or letter (e.g., Detectable label 1, bead (ii), etc.). Where this nomenclature is used, these numbers and letters are meant to distinguish the item from other items of the same type (e.g., bead (i) vs. bead (ii)), and are not meant to associate a specific property with the number or letter. Any methods, devices and materials similar or equivalent to those described herein can be used in the practice of this invention. The following definitions are provided to facilitate understanding of certain terms used frequently herein and are not meant to limit the scope of the present disclosure.

Multiplex assays are analyses that simultaneously measure the levels of more than one analyte in a single sample. Multiplex assay methods and reagents are described, e.g., in U.S. Pat. No. 6,872,578 and WO2008148883 (each of which is hereby incorporated by reference in its entirety). In the context of this application, the analytes to be measured are antibodies specific to the peptides or proteins affixed to the solid substrates disclosed herein. In preferred embodiments, the antibodies are of the IgG and/or IgM classes of antibodies.

The term "solid support" or "substrate" (and grammatical equivalents of these terms) are used to denote a solid inert surface or body to which an agent, such as an antibody or a peptide or protein can be immobilized. These terms ("solid support" or "substrate" (and grammatical equivalents of these terms)) may be used interchangeably. Non-limiting examples of a solid support or substrate include plastic, polystyrenes, nitrocellulose, membranes, chips, and particles. If solid supports other than particles are used, for instance, glass, polymeric or silica chips (such as microchips), plates, slides, etc., the peptides and/or proteins (target analytes) disclosed herein can be immobilized on the surface of the support at specific locations (e.g., in specific wells of a plate (e.g., microtiter plate) or at specific locations on a chip, microchip, plate or slide). Thus, it is possible to differentiate antibodies within a sample by the location at which specific binding between antibodies in a sample and the peptides and/or proteins disclosed herein occurs on the surface of the support.

Alternatively, lateral flow immunoassays can be performed in a manner analogous to those disclosed in U.S. Pat. Nos. 5,851,776 and 6,777,190 (each of which is hereby incorporated by reference in their entireties and which relate to lateral flow chromatographic assays on a membrane or other porous or non-porous materials). As discussed above, peptides and/or proteins (target analytes) disclosed herein are immobilized at discrete locations on the membrane or other porous or non-porous material (each location being specific for a particular antigen/target analyte) and then contacted with a biological sample containing antibodies that specifically bind to the disclosed peptides and/or proteins (target analytes). The specific binding to antibodies to the peptides and/or proteins that are immobilized at discrete locations on the membrane or other porous or non-porous material is then detected using conventional methods. The term "particle" is used herein to refer to a solid or semisolid body, often with linear dimensions on the micron scale (i.e., less than about 100 microns), of any shape or surface texture. Except as noted, the term is used interchangeably with "particle," which refers to a micron scale particle, and "bead," which refers to particles that are spherical or near-spherical in shape, often polymeric in composition. Where used in this application, the terms "particle" and "bead" (and grammatical equivalents of these terms) can be interchanged without altering the context of the passages within this application).

The term "immobilized" as used herein denotes a molecular-based coupling that is not significantly de-coupled under the conditions imposed during the steps of the assays described herein. Such immobilization can be achieved through a covalent bond, a non-covalent bond, an ionic bond, an affinity interaction (e.g., avidin-biotin or polyhistidine-$Ni^{++}$), or any other chemical bond.

Immobilization of the various combinations of peptides and/or proteins disclosed in this application can be performed by covalent or non-covalent immobilization on a substrate. For example, non-covalent immobilization can be non-specific (e.g., non-specific binding of a combination of one or more peptides and/or proteins to a polystyrene surface). Specific or semi-specific binding to a substrate can be achieved by the peptide and/or protein having a moiety that enables covalent or non-covalent binding of the peptide and/or protein to the substrate that is coated with a ligand that binds to the moiety. For example, the moiety can be a biotin or biotinyl group or an analogue thereof bound to an amino acid group of the peptide, such as 6-aminohexanoic acid, and the ligand is then avidin, streptavidin or an analogue thereof. Alternatively, the moiety can be a His-His-His-His-His-His peptide (SEQ ID NO:1) and the substrate can be derivatized with a Nitrilotriacetic Acid derivative (NTA) charged with $Ni^{++}$ ions. Various substrates suitable for use in the disclosed methods include, and are not limited to, magnetic beads, polystyrene beads, latex beads, beads comprising co-polymers such as styrene-divinyl benzene; hydroxylated styrene-divinyl benzene; polystyrene; carboxylated polystyrene; carbon black; non-activated, polystyrene or polyvinyl chloride activated glass; epoxy-activated porous magnetic glass; gelatin or polysaccharide particles; protein particles or red blood cells. In other embodiments, the substrate can be the floor or wall of a microtiter well; a filter surface or membrane (e.g., a nitro-cellulose membrane or a PVDF (polyvinylidene fluoride) membrane, such as an Immobilon membrane); a hollow fiber; a beaded chromatographic medium (e.g., an agarose or polyacrylamide gel); a magnetic bead; a fibrous cellulose matrix; an HPLC matrix; an FPLC matrix; or any other suitable carrier, support or surface. In one embodiment of the invention, one or more peptides and/or proteins disclosed herein are immobilized onto polystyrene beads (microspheres), wherein each peptide or protein is immobilized onto a bead with a unique detectable physical parameter, and are analyzed by the xMAP® technology developed by Luminex Technology (Austin, Tex.) and described in their world wide web site luminexcorp.com. Such assays may be referred to as "multiplex immunoassays" and are discussed in detail below.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices, chips, microchips, lateral flow substrates dipsticks and immunocapillary or immunochromatographic immunoassay devices.

The terms "receptacle," "vessel," "tube," "well," etc. refer to a container that can hold reagents or an assay. If the receptacle is in a kit and holds reagents, it will typically be closed or sealed. If the receptacle is being used for an assay, it will typically be open or accessible during steps of the assay.

The term "biological sample" encompasses a variety of sample types obtained from an organism. The term encompasses bodily fluids such as blood, blood components, saliva, serum, plasma, cerebro-spinal fluid (CSF), urine and other liquid samples of biological origin, solid tissue biopsy, tissue cultures, or supernatant taken from cultured patient cells. In the context of the present disclosure, the biological sample is typically a bodily fluid with detectable amounts of antibodies, e.g., blood or a blood component (e.g., plasma or serum) or CSF. The biological sample can be processed prior to assay, e.g., to remove cells or cellular debris. The term encompasses samples that have been manipulated after their procurement, such as by treatment with reagents, solubilization, sedimentation, or enrichment for certain components.

The term "antibody" as used herein refers to a polypeptide encoded by an immunoglobulin gene or immunoglobulin genes, or fragments thereof, which specifically bind and recognize an analyte (antigen). The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively. An example of a structural unit of immunoglobulin G (IgG antibody) is a tetramer. Each such tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively.

Antibodies exist as intact immunoglobulins or as well-characterized fragments produced by digestion of intact immunoglobulins with various peptidases. Thus, for example, pepsin digests an antibody near the disulfide linkages in the hinge region to produce F(ab')$_2$, a dimer of Fab which itself is a light chain joined to VH-CH1 by a disulfide bond. The F(ab')2 dimer can be reduced under mild conditions to break the disulfide linkage in the hinge region, thereby converting the F(ab')$_2$ dimer into two Fab' monomers. The Fab' monomer is essentially an Fab with part of the hinge region (see, Paul (Ed.), Fundamental Immunology, Third Edition, Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies.

Antibodies are commonly referred to according their targets. While the nomenclature varies, one of skill in the art will be familiar and understand that several names can be applied to the same antibody. For example, an antibody specific for IgM can be called "anti-IgM," "IgM antibody," "anti-IgM antibody," etc.

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). In the context of this application the term "antigen," "immunogen," "antibody target," "target analyte," and grammatical equivalents thereof refer to *Borrelia* specific peptides and proteins selected from pFlaB-mV, pErp59-mV and pP35-mV, p58, outer surface protein C (Osp C) (e.g., Osp C type B or type I protein) and DbpA. One of skill will understand that the term does not indicate that the molecule is immunogenic in every context, but simply indicates that it specifically binds to an antibody. The peptide and protein sequences of different target antigens used for the detection of *Borrelia* specific total (IgG and IgM) antibodies disclosed in this application are as follows:

a) pFlaB-mV (a synthetic fusion peptide comprising 14 amino acids of the 41 kDa flagellin antigen (FlaB) and 20 amino acids of the modified VlsE sequence):

```
                                    (SEQ ID NO: 2)
CVQEGVQQEGAQQPGGGMKKNDQIVAAIALRGVA;
``` b) pErp59-mV (a synthetic fusion peptide comprising 15 amino acids of the outer surface protein ErpP and 20 amino acids of the modified VlsE sequence):

```
                                    (SEQ ID NO: 3)
KIEFSKFTVKIKNKDGGGMKKNDQIVAAIALRGVA;
``` c) pP35-mV (a synthetic fusion peptide comprising 15 amino acids of the antigenic protein P35 and 20 amino acids of the modified VlsE sequence):

```
                                    (SEQ ID NO: 4)
DTGSERSIRYRRRVYGGGMKKNDQIVAAIALRGVA;
``` d) Outer surface protein C (OspC)-type B:

```
                                              (SEQ ID NO: 5)
MTLFLFISCNNSGKDGNTSANSADESVKGPNLTEISKKITDSNAVLLAV

KEVEALLSSIDELAKAIGKKIKNDGSLDNEANRNESLLAGAYTISTLIT

QKLSKLNGSEGLKEKIAAAKKCSEEFSTKLKDNHAQLGIQGVTDENAKK

AILKANAAGKDKGVEELEKLSSLESLSKAAKEMLANSVKELTSPVV;
``` e) Outer surface protein C (OspC)-type I:

```
                                              (SEQ ID NO: 6)
MTLFLFISCNNSGKDGNTSANSADESVKGPNLTEISKKITESNAVVLAV

KEVETLLTSIDELAKAIGKKIKNDVSLDNEADHNGSLISGAYLISNLIT

KKISAIKDSGELKAEIEKAKKCSEEFTAKLKGEHTDLGKEGVTDDNAKK

AILKTNNDKTKGADELEKLFESVKNLSKAAKEMLTNSVKELTSP;
``` f) Decorin binding protein A (DbpA) from *B. afzelii*:

```
                                              (SEQ ID NO: 7)
MIKYNKIILTLTLLASLLAACSLTGKARLESSVKDITNEIEKAIKEAE

DAGVKTDAFTETQTGGKVAGPKIRAAKIRVADLTIKFLEATEEETITF

KENGAGEDEFSGIYDLILNAAKAVEKIGMKDMTKTVEEAAKENPKTTA

NGIIEIVKVMKAKVENIKEKQTKNQK;
``` and g) Membrane protein P58 from *B. garinii*:

```
                                              (SEQ ID NO: 8)
MKLQKLLFSVIFFLTFLCCNKEEKKEGISFKISLGSEPSSLDPQLADD

NVGSKMIDTMFRGLITGDPNTGGNKPGLAKSWDISPDGTVYTFTLREK

IIWSDGVAITAEGIRKSYLRILNKETGSNYAEMVKSTIKNGQKYFDGQ

VSDSELGIRAIDEKTLEITLESPKPYFIDMLVHQSFIPIPIHIAEKYG

QSWTSPENIVTSGPFKLKERIPNEKYVVEKNDKYYNSNQVEVQEITFY

TTNDSSTAYKMYENKELDAIFGSIPPDLIKDLKLRSDYYSSAVNAIYF
```

-continued

```
YAFNTYIKPLDNVKVRKALTLAIDRETLTYKVLDNGTTPTRRIAPNFS

SYSYAKNLELFNPEIAKTLLAEAGYPNGNGFPILKLKYNTSEAHKKIC

EFIQNQWKKILNIDVELENEEWTTYLNTRSNGNYEIARAGWIGDYADP

LTFLSIFTQGYTQFSSHNYSSPEYNELIKKSDLELDPIKRQDILRKAE

EIIIEKDFPIAPIYIYGNSYLFRNDKWTGWNTNITERFDLSQLKLKNK.
```

The construction of the chimeric (fusion) peptides as well as the cloning and expression of recombinant proteins has been described previously (see references 9-12, each of which is hereby incorporated by reference in its entirety). Additionally, while the application provides specific reference to Osp C types B and I from *Borrelia burgdorferi* strains, other types of Osp C (e.g., Osp C types A, C-H and J-U) can be used interchangeably with Osp C type B and OspC type I within the context of the invention. Thus, Osp C type B and/or Osp C type I can be substituted with any one of the other Osp C proteins (e.g., types A, C-H or J-U). The sequences for these types of Osp C are known in the art and can be accessed at, for example, the web site borreliabase-.org. Additionally, *Borrelia burgdorferi* Osp C polypeptide sequences can be accessed at the GenBank (ncbi.nlm.nih-.gov/genbank/) and UniProt (uniprot.org/uniprot/) web sites.

Various embodiments of the disclosed invention relate to multivalent antigens. In this context, a multivalent antigen is composed of two or more of the aforementioned *Borrelia* specific peptides and proteins selected from pFlaB-mV, pErp59-mV and pP35-mV, p58, outer surface protein C (Osp C) type B, outer surface protein C (Osp C) type I and DbpA. The multivalent antigens can be composed of two or more of the same antigen (e.g., pFlaB-mV-pFlaB-mV) or different antigens (e.g., pFlaB-mV-pErp59-mV). Exemplary embodiments of multivalent antigens include pFlaB-mV-OspC type B; pFlaB-mV-OspC type I; pErp59-mV-OspC type B; pErp59-mV-OspC type I; pFlaB-mV-p58; and pFlaB-mV-DbpA.

A number of flexible linkers can be used to replace in the construction of the multivalent antigens discussed above. The linker sequence should not be significantly deleterious to the recognition of the antigen by an antibody specific for the antigen and exemplary liners include flexible Gly-Ser linkers. Such linkers are known to those of skill in the art and a non-limiting Gly-Ser example includes GGSGSG (SEQ ID NO: 9). Additional Gly-Ser linkers include GSTSGSGKPGSGEGSTKG (SEQ ID NO: 10) and SGRAHAG (SEQ ID NO: 11). Other flexible linkers are composed of $(Gly)_n$, where n=1 to 10 (e.g., n=1, 2, 3, 4, 5, 6, 7, 8, 9, or 10); $(Ser)_n$, where n=1 to 10 (e.g., n=1, 2, 3, 4, 5, 6, 7, 8, 9, or 10; $(Ala)_n$, where n=1 to 10 (e.g., n=1, 2, 3, 4, 5, 6, 7, 8, 9, or 10; $(Gly\text{-}Ser)_n$, where n=1 to 10 (e.g., n=1, 2, 3, 4, 5, 6, 7, 8, 9, or 10; $(Gly\text{-}Ser\text{-}Ser\text{-}Gly)_n$, where n=1 to 10 (e.g., n=1, 2, 3, 4, 5, 6, 7, 8, 9, or 10; SEQ ID NO: 12); $(Gly\text{-}Ser\text{-}Gly)_n$, where n=1 to 10 (e.g., n=1, 2, 3, 4, 5, 6, 7, 8, 9, or 10; $(Gly\text{-}Ser\text{-}Ser)_n$, where n=1 to 10 (e.g., n=1, 2, 3, 4, 5, 6, 7, 8, 9, or 10; $(Gly\text{-}Ala)_n$, where n=1 to 10 (e.g., n=1, 2, 3, 4, 5, 6, 7, 8, 9, or 10), or any combination thereof.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The terms "specific for," "specifically binds," and grammatically equivalent terms refer to a molecule (e.g., antibody or antibody fragment) that binds to its target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a given antibody target will typically bind the antibody target with at least a 2-fold greater affinity than a non-antibody target. Specificity can be determined using standard methods, e.g., solid-phase ELISA immunoassays (see, e.g., Harlow & Lane, *Using Antibodies, A Laboratory Manual* (1998) for a description of immunoassay formats and conditions that can be used to determine specific immunoreactivity).

The term "binds" with respect to an antibody target (e.g., antigen, analyte), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, enzymes acting on a substrate (e.g., horseradish peroxidase), digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

The term "positive," when referring to a result or signal, indicates the presence of an analyte or item that is being detected in a sample. The term "negative," when referring to a result or signal, indicates the absence of an analyte or item that is being detected in a sample. Positive and negative are typically determined by comparison to at least one control, e.g., a threshold level that is required for a sample to be determined positive, or a negative control (e.g., a known blank). A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters, and will understand which controls are valuable in a given situation and be able to analyze data based on comparisons to control values. Controls are also valuable for determining the significance of data. For example, if values for a given parameter are variable in controls, variation in test samples will not be considered as significant.

A "calibration control" is similar to a positive control, in that it includes a known amount of a known analyte. In the case of a multiplex assay, the calibration control can be designed to include known amounts of multiple known analytes. The amount of analyte(s) in the calibration control can be set at a minimum cut-off amount, e.g., so that a higher amount will be considered "positive" for the analyte(s), while a lower amount will be considered "negative" for the analyte(s). In some cases, multilevel calibration controls can be used, so that a range of analyte amounts can be more accurately determined. For example, an assay can include calibration controls at known low and high amounts, or known minimal, intermediate, and maximal amounts.

The term "diagnosis" refers to a relative probability that a subject has an infection, disorder or disease. Similarly, the term "prognosis" refers to a relative probability that a certain future outcome may occur in the subject. For example, in the context of the present disclosure, prognosis can refer to the likelihood that an individual has been infected by a *Borrelia* spp. and has, or will develop, Lyme disease. The terms are not intended to be absolute, as will be appreciated by any one of skill in the field of medical diagnostics.

"Subject," "patient," "individual" and grammatical equivalents thereof are used interchangeably and refer to, except where indicated, mammals such as humans and non-human primates, as well as rabbits, felines, canines, rats, mice, squirrels, goats, pigs, deer, and other mammalian species. The term does not necessarily indicate that the subject has been diagnosed with a particular disease, but typically refers to an individual under medical or veterinary supervision. A patient can be an individual that is seeking treatment, monitoring, adjustment or modification of an existing therapeutic regimen, etc.

The term "peptide" (and grammatical equivalents thereof) includes peptides composed of two or more distinct *Borrelia* specific peptides (also referred to as a "chimeric peptide" or "chimeric peptides") and peptides composed of amino acids obtained from a single *Borrelia* polypeptide.

As discussed above, the present invention relates to the development of a novel immunoassay for the detection of *Borrelia* antibodies in patient samples suspected of Lyme disease (e.g., patients with acute infection by *Borrelia* bacterial cells, e.g., *B. burgdorferi, B. garinii* or *B. afzelii*). "Acute infection" refers to the first stage of infection soon after patient becomes infected by *B. burgdorferi, B. garinii* or *B. afzelii*. The acute infection may be of a brief or prolonged duration. In general, erythema migrans (EM) lesion(s), appears between 1-7 days after a tick bite and infection by *burgdorferi, B. garinii* or *B. afzelii*. The formation of antibodies follow thereafter, however, some patients exhibit antibodies without the presence of EM. The disclosed immunoassays are designed to measure antibodies (e.g., IgM and/or IgG antibodies) in patients with early and/or established infection. Based on well characterized CDC and European samples, the disclosed immunoassays are able to detect antibodies associated with acute infection.

The immunoassay can be performed via a standard immunoassay using ELISA, lateral flow, magnetic assays with manual or using automated platforms. Particularly, the disclosed immunoassay uses one or more *Borrelia* specific peptide selected from pFlaB-mV, pErp59-mV and pP35-mV, p58, outer surface protein C (Osp C) (e.g., Osp C type B or type I) and DbpA. In other words, the antigens used in the disclosed immunoassays are selected from the group consisting of pFlaB-mV, pErp59-mV and pP35-mV, p58, outer surface protein C (Osp C) (e.g., Osp C type B or type I), DbpA and any combination of said antigens (e.g., any combination of two, three, four, five, six or seven of the antigens).

Yet other embodiments provide an immunoassay uses a combination of antigens selected from two separate groups of antigens. In such embodiments, the first group of antigens is selected from the group consisting of pFlaB-mV, pErp59-mV, pP35-mV and combinations thereof. The second group of antigens used in the immunoassay is selected from the group consisting of p58, outer surface protein C (Osp C) (e.g., Osp C type B or type I), DbpA and combinations thereof.

Another embodiment provides an immunoassay in which a single *Borrelia* specific peptide or outer surface protein selected from pFlaB-mV, pErp59-mV and pP35-mV, p58, outer surface protein C (Osp C) (e.g., Osp C type B or type I), and DbpA is immobilized on a substrate. As would be apparent to those skilled in the art, various of the *Borrelia* specific peptides disclosed in this application can be chimeric peptides (e.g., pFlaB-mV, pErp59-mV and pP35-mV). Thus, the disclosed immunoassay comprises contacting a substrate to which one or more *Borrelia* specific peptide or outer surface protein selected from pFlaB-mV, pErp59-mV and pP35-mV, p58, outer surface protein C (Osp C) (e.g., Osp C type B or type I) and DbpA have been immobilized under conditions effective to bind antibodies found in a biological sample to the immobilized *Borrelia* specific peptide or outer surface protein. Antibodies bound to the *Borrelia* specific peptide attached to a substrate can then be detected by a species specific anti-IgM, anti-IgG, anti-IgA, anti-IgD or anti-IgE antibody that is labeled (e.g., anti-human, anti-rabbit, anti-canine, anti-rat, anti-mouse, anti-squirrel, anti-goat, anti-pig or anti-deer antibody). For example, anti-IgG-PE and/or anti-IgM-PE reporters can be used to detect and/or quantify the *Borrelia* specific antibodies in biological samples obtained from individuals suspected of infection by *Borrelia* spp. In certain preferred embodiments, the species specific antibodies are anti-human antibodies.

The protein and peptide antigens disclosed herein (e.g., pFlaB-mV, pErp59-mV and pP35-mV, p58, outer surface protein C (Osp C) (e.g., Osp C type B or type I) and DbpA singly or in any combination) can be immobilized on a solid support via covalent or non-covalent bonding. In embodiments where the protein and peptide antigen is covalently immobilized on the substrate, carboxylated substrates, such as particles, plastics, polystyrenes or beads, are activated and esterified before adding the *Borrelia* specific peptide and protein antigen(s). Carboxyl activation is achieved using a water soluble carbodiimide, such as 1-cyclohexyl-3-(2-morpholinoethyl) carbodiimide (CMC). Esterification is achieved using NHS, NHSS or HOBt or other suitable reagents. After carboxyl activation and esterification, the *Borrelia* antigen(s) are added to the actived surface in buffers with pH between 6-10 (an example of which is sodium acetate buffer pH 5.1, phosphate buffer pH 7.0 with or without detergent (e.g., CHAPS)). After the coupling, the substrate (e.g., beads) are blocked in buffers containing protein blockers such as BSA, mouse IgG, bovine gamma globulin (BGG) or animal serum (goat, horse, murine). The protein blocker(s) can be present in an amount ranging from 0.1-10 weight/volume percent. The blocked antigen coupled substrates can then be washed with an appropriate buffer and used in a desired immunoassay format.

As discussed above, the disclosed invention is directed to an immunoassay method, which includes taking a sample of body fluid or tissue (e.g., a biological sample) likely to contain antibodies; contacting (reacting) the biological sample with a peptide or combination of peptides and proteins disclosed herein, under conditions effective for the formation of a specific peptide-antibody complex (sometimes referred to as specific binding of the peptide and the antibody or "an immunocomplex" of a given peptide/protein and antibodies that specifically bind the peptide/protein); and assaying the contacted (reacted) sample for the presence of an antibody-peptide immunocomplex (e.g., determining the amount of an antibody-peptide complex).

In various embodiments, the disclosed method relates to a diagnostic method that comprises taking a sample of body fluid or tissue (a biological sample) likely to contain antibodies (IgG, IgE, IgD, IgM, or IgA isotypes) and detecting and/or quantifying the presence of the antibodies within the biological sample. Generally, IgM and/or IgG antibodies are detected (although antibodies of other isotypes may also be detected). In various embodiments, the biological sample is a serum or plasma sample derived from a venous blood sample. Other body fluids, such as cerebro-spinal fluid (CSF), saliva, gastric secretions, mucus, etc., that are known to contain antibodies may also be referred to as a biological sample and used in the disclosed immunoassays.

In various embodiments, the assay may comprise immobilizing antibody(s) in the biological sample on a substrate (forming a substrate coated with antibody), adding one or more peptide and/or protein disclosed herein to the antibody coated substrate, and then detecting antibody bound to the peptide or protein. The antibody present in the biological sample can be detected by using a labeled peptide or protein or by adding a labeled antibody that specifically binds to the peptide or protein.

In particular embodiments, multiplex immunoassays can be used to detect the presence of one or more of the peptides and/or proteins (analyte) disclosed herein (e.g., pFlaB-mV, pErp59-mV and pP35-mV, p58, outer surface protein C (Osp C) (e.g., Osp C type B or type I) and DbpA). Thus, the presently described immunoassays involve detection of more than one analyte in a single assay, and are, thus, referred to as multiplex assays. The presently described assays include components for immobilizing single or multiple analytes on distinguishable solid supports so that each of the analytes can be identified and quantified by flow cytometry. Assay components and considerations include the solid supports and how to distinguish the different types of solid supports from one another (e.g., labels or other differentiation parameters), components to specifically immobilize the desired analyte(s) and remove other sample materials, and labels for detecting and quantifying the desired analytes.

The presently described multiplex assays involve use of a solid support, typically particles or beads. For detection by flow cytometry, particles or beads that emit high levels of autofluorescence should be avoided since this will increase background signal and potentially render them unsuitable. Particles or beads created by standard emulsion polymerization from a variety of starting monomers generally exhibit low autofluorescence, while those that have been modified to increase porosity ("macroporous" particles) exhibit high autofluorescence. Autofluorescence in such particles or beads further increases with increasing size and increasing percentage of divinylbenzene monomer. Within these limitations, the size range of the particles or beads can vary and particular size ranges are not critical. In most cases, the aggregated size range of the particles or beads lies within the range of from about 0.3 micrometer to about 100 micrometers in particle or bead diameter, e.g., within the range of from about 0.5 micrometer to about 40 micrometers.

Magnetic particles or beads are commonly used in the art, and can make separation and wash steps more convenient for the presently described assays. "Magnetic particles," "magnetically responsive material," "magnetic beads," and like terms denote a material that responds to a magnetic field. Magnetically responsive materials include paramagnetic materials (e.g., iron, nickel, and cobalt, as well as metal oxides such as $Fe_3O_4$, $BaFe_{12}O_{19}$, CoO, NiO, $Mn_2O_3$, $Cr_2O_3$, and CoMnP), ferromagnetic materials, ferrimagnetic materials, and metamagnetic materials. Rather than constituting the entire particle or bead, the magnetically responsive material typically constitutes one component of the microparticle or bead, while the remainder consists of a polymeric material which can be chemically derivatized to permit attachment of an assay reagent (e.g., antigen/analyte or antibody). Methods of, and instrumentation for, applying and removing a magnetic field as part of an assay are known to those skilled in the art and reported in the literature. Examples of literature reports are Forrest et al., U.S. Pat. No. 4,141,687; Ithakissios, U.S. Pat. No. 4,115,534; Vlieger et al., *Analytical Biochemistry* 205:1-7 (1992); Dudley, *Journal of Clinical Immunoassay* 14:77-82 (1991); and Smart, *Journal of Clinical Immunoassay* 15:246-251 (1992).

The polymeric matrix that forms the microparticle or bead can be any material that is compatible with the presently described multiplex assay. The matrix should be inert to the components of the biological sample and to the assay reagents, have minimal autofluorescence, be solid and insoluble in the sample and in any other reagents or washes used in the assay, and capable of affixing an assay reagent to the microparticle. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle.

Functional groups for attachment of the assay reagent (e.g., antigen/analyte or antibody) can be incorporated into the polymer structure by conventional means. Examples of suitable functional groups are amine groups, ammonium groups, hydroxyl groups, carboxylic acid groups, and isocyanate groups. The assay reagent is typically covalently bound to the solid phase surface, either directly or indirectly, e.g., with a linking group. Linking groups can be used as a means of increasing the density of reactive groups on the solid phase surface and decreasing steric hindrance to increase the range and sensitivity of the assay, or as a means of adding specific types of reactive groups to the solid phase surface to broaden the range of types of assay reagents that can be affixed to the solid phase. Examples of suitable useful linking groups are polylysine, polyglycine, polyaspartic acid, polyglutamic acid and polyarginine.

Particles or beads of different types in a multiplex assay can be distinguished from one another, e.g., by size, weight, light scatter or absorbance, reflectance, shape, or label, e.g., fluorescent (dye) label. Where particle or bead size is used as a differentiation factor (distinguishing characteristic), the widths of the size subranges and the spacing between mean diameters of adjacent subranges are selected to permit differentiation of different types of particles or beads by flow cytometry, as will be apparent to those skilled in the use of and instrumentation for flow cytometry. Typically, a subrange for a given mean diameter is about ±5% CV or less of the mean diameter, where CV is the coefficient of variation and is defined as the standard deviation of the particle or bead diameter divided by the mean particle diameter times 100 percent. The mean diameters of subranges for different types of particles are generally spaced apart by at least about 6% of the mean diameter of one of the subranges, e.g., at least about 8% or 10% of the mean diameter of one of the subranges.

Light scatter can also be used to distinguish different types of particles or beads. Side angle light scatter varies with particle or beads size, granularity, absorbance and surface roughness, while forward angle light scatter is mainly affected by size and refractive index. Varying any of these qualities can result in light scatter differences that can serve as a means of distinguishing the various groups or particles or beads.

Still another example of a differentiation parameter is absorbance. When light is applied to particles or beads, the absorbance of the light by the particles or beads is indicated mostly by a change in the strength of the laterally (side-angle) scattered light while the strength of the forward-scattered light is relatively unaffected. Consequently, the difference in absorbance between various colored dyes associated with the particles or beads is determined by observing differences in the strength of the laterally scattered light.

Other physical parameters that can be used as differentiation parameters to distinguish the particles or beads of one group from those of another include excitable fluorescent dyes or colored dyes that impart different emission spectra and/or scattering characteristics to the particles or beads. Alternatively, different concentrations of one or more fluorescent dyes can be used for distinguishing or differentiating particles or beads.

When the distinguishable characteristic is a fluorescent dye or color, it can be coated on the surface of the particle or bead, embedded in the particle or bead, or bound to the molecules of the particle or bead material. Thus, fluorescent particles or beads can be manufactured by combining the polymer material with the fluorescent dye, or by impregnating the particle or bead with the dye. Particles or beads with dyes already incorporated and thereby suitable for use in the present invention are commercially available, from suppliers such as Spherotech, Inc. (Libertyville, Ill., USA) and Molecular Probes, Inc. (Eugene, Oreg., USA). A list of vendors of flow cytometric products can be found, e.g., at the web site molbio.princeton.edu/facs/FCMsites.html.

Labels can be any substance or component that directly or indirectly emits or generates a detectable signal. In some embodiments, the labels are fluorophores, many of which are reported in the literature and thus known to those skilled in the art, and many of which are readily commercially available. Literature sources for fluorophores include Cardullo et al., *Proc. Natl. Acad. Sci. USA* 85: 8790-8794 (1988); Dexter, *J. of Chemical Physics* 21: 836-850 (1953); Hochstrasser et al., *Biophysical Chemistry* 45: 133-141 (1992); Selvin, *Methods in Enzymology* 246: 300-334 (1995); Steinberg, *Ann. Rev. Biochem.,* 40: 83-114 (1971); Stryer, *Ann. Rev. Biochem.* 47: 819-846 (1978); Wang et al., *Tetrahedron Letters* 31: 6493-6496 (1990); and Wang et al., *Anal. Chem.* 67: 1197-1203 (1995). The following are non-limiting examples of fluorophores that can be used as labels:

4-acetamido-4'-isothiocyanatostilbene-2,2'disulfonic acid; acridine; acridine isothiocyanate; 5-(2'-aminoethyl) aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin; 7-amino-4-methyl-coumarin (AMC, Coumarin 120); 7-amino-4-trifluoromethylcoumarin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4methylcoumarin; diethylenetriamine pentaacetate; 4,4'-diisothiocyanatodihydro-stilbene-2,2- disulfonic acid; 4,4'-diisothiocyanatostilbene-2,2'-disulfonic acid; 5-[dimethylamino] naphthalene-1-sulfonyl chloride (DNS, dansylchloride); 4-(4'-dimethylaminophenylazo)benzoic acid (DABCYL); 4-dimethylaminophenylazophenyl-4'-isothiocyanate (DABITC); eosin; eosin isothiocyanate; erythrosin B; erythrosin isothiocyanate; ethidium; 5-carboxyfluorescein (FAM); 5-(4,6-dichlorotriazin-2-yl)aminofluorescein (DTAF); 2',7'-dimethoxy-4'5'-dichloro-6-carboxyfluorescein (JOE); fluorescein; fluorescein isothiocyanate; fluorescamine; IR144; IR1446; Malachite Green isothiocyanate; 4-methylumbelliferone; ortho cresolphthalein; nitrotyrosine; pararosaniline; Phenol Red; phycoerythrin (including but not limited to B and R types); o-phthaldialdehyde; pyrene; pyrene butyrate; succinimidyl 1-pyrene butyrate; quantum dots; Reactive Red 4 (Cibacron™ Brilliant Red 3B-A); 6-carboxy-X-rhodamine (ROX); 6-carboxyrhodamine (R6G); lissamine rhodamine B sulfonyl chloride rhodamine; rhodamine B; rhodamine 123; rhodamine X isothiocyanate; sulforhodamine B; sulforhodamine 101; sulfonyl chloride derivative of sulforhodamine 101 (TEXAS RED); N,N,N', N'-tetramethyl-6-carboxyrhodamine (TAMRA); tetramethyl rhodamine; tetramethyl rhodamine isothiocyanate (TRITC); riboflavin; rosolic acid; and lanthanide chelate derivatives.

Particular fluorophores for use in the disclosed immunoassays include fluorescein, fluorescein isothiocyanate, phycoerythrin, rhodamine B, and TEXAS RED (sulfonyl chloride derivative of sulforhodamine 101). Any of the fluorophores in the list preceding this paragraph can be used in the presently described assays, either to label the particle or bead, or to label a binding agent (e.g., an antibody or streptavidin). Fluorochromes can be attached by conventional covalent bonding, using appropriate functional groups on the fluorophores and on the particle or bead or binding agent (e.g., an antibody or streptavidin). The recognition of such groups and the reactions to form the linkages will be readily apparent to those skilled in the art. Other labels that can be used in place of the fluorophores are radioactive labels and enzyme labels. These are likewise known in the art. Flow cytometry methods and instrumentation are known in the art. Descriptions of instrumentation and methods can be found, e.g., in Introduction to Flow Cytometry: A Learning Guide (2000) Becton, Dickinson, and Company; McHugh, "Flow Microsphere Immunoassay for the Quantitative and Simultaneous Detection of Multiple Soluble Analytes," Methods in Cell Biology 42, Part B (Academic Press, 1994).

The disclosed invention also pertains to kits and compositions for the detection of *Borrelia* infection in a subject. The multiplex assay disclosed herein provides for the detection and/or quantification of immunoglobulin G (IgG) antibodies and/or IgM antibodies specific for *Borrelia* peptides and proteins. The multiplex assay disclosed herein can detect and/or quantify the amount of *Borrelia* specific IgG or IgM antibodies present in a biological sample. The multiplex assays disclosed herein can also detect the presence of total amount of *Borrelia* specific antibody present in a biological sample.

Various of the presently described assays offer detection in at least two dimensions, e.g., the identity of the immobilizing bead (e.g., beads bearing a single *Borrelia* specific peptide or protein or any combination of the *Borrelia* specific peptides and/or proteins disclosed herein, and the presence and amount of antibody bound to the *Borrelia* specific peptide and/or proteins immobilized on the beads. This multidimensional aspect allows for a multiplex format, so that more than one analyte can be detected in a single assay. Moreover, as described below, the inventors have shown that the presently described multiplex assay results correlate with infection status of known patient samples and permit the detection of *Borrelia* infection in a subject.

Thus, one aspect of the invention provides for combinations of substrate populations. These substrate combinations are made up of two, three, four, five, six or seven distinct and unique detectable physical parameters (e.g., dye signatures), each distinct and unique detectable physical parameter being associated with a single substrate. By way of example, various substrate-detectable parameters are set forth Substrate/Antigen Combination tables set forth below. For ease of reference, the combinations are set forth using designations A, B, C, D, E, F and G. As would be apparent to one skilled in the art, these designations are arbitrary and any peptide/protein can be combined with any desired distinct and unique dye signature. Thus, for the purposes of illustration, the following designations are used: A=pFlaB-mV-substrate-detectable physical parameter 1; B=pErp59-mV-substrate-detectable physical parameter 2; C=pP35-mV-substrate-detectable physical parameter 3; D=OspC-type I-substrate-detectable physical parameter 4; E=OspC-type B-substrate-detectable physical parameter 5; F=DbpA-substrate-detectable physical parameter 6; and G=p58-substrate-detectable physical parameter 7. As discussed above, the detectable parameter can be a unique dye signature and the population of beads can have up to seven unique and distinct dye signatures.

Figure 2:
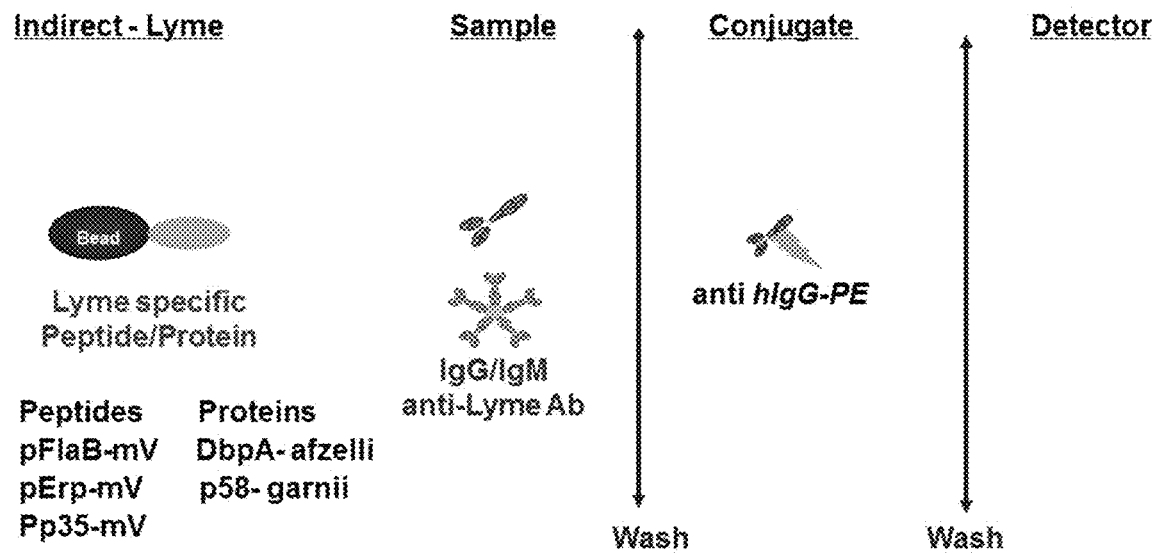
Figure 3:
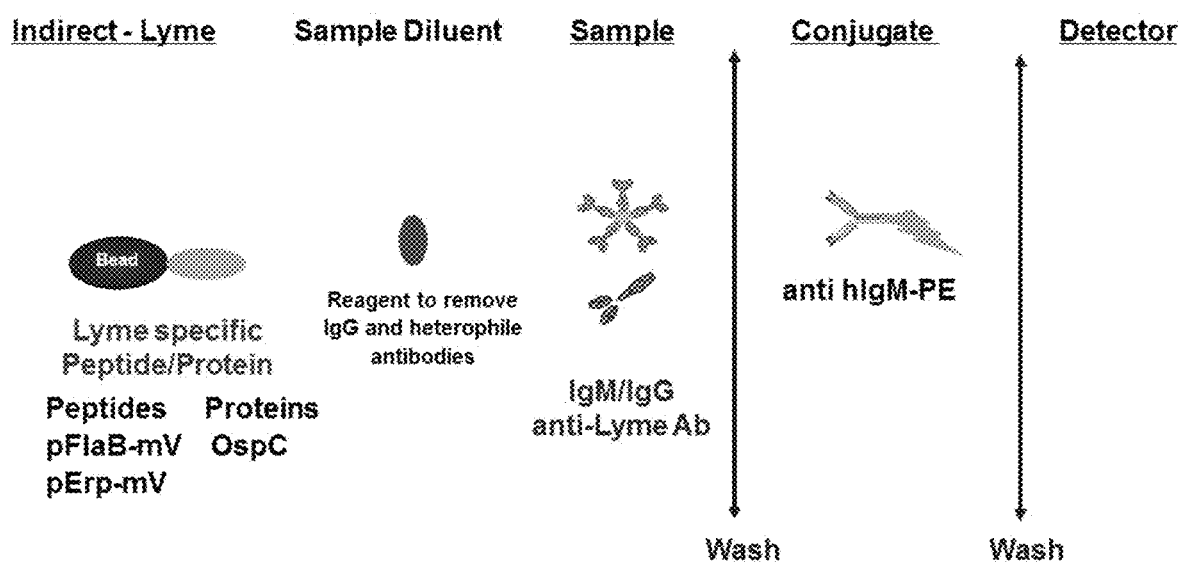

In some embodiments, the presence and amount of each of the antibody isotypes are measured in the same single receptacle or vessel (tube, well, cuvette, etc.) in the presence of beads. As discussed above, bead carries a specific detectable physical parameter (e.g., dye signature), and one or more *Borrelia* specific peptide or protein. Thus, the beads can carry a single peptide or protein selected from pFlaB-mV, pErp59-mV and pP35-mV, p58, outer surface protein C (Osp C) type B, outer surface protein C (Osp C) type I and DbpA. Alternative embodiments provide beads carrying any one of the two, three, four, five, six or seven peptide/protein combinations disclosed within this application. However, it is preferred that a single peptide or protein selected from pFlaB-mV, pErp59-mV and pP35-mV, p58, outer surface protein C (Osp C) type B, outer surface protein C (Osp C) type I and DbpA be associated with a bead that carries a specific detectable physical parameter (e.g., dye signature). In other words, each of the seven disclosed peptides or proteins will be associated with beads that provide a unique specific detectable physical parameter (e.g., dye signature) giving rise to a population of beads having seven distinct detectable physical parameters (e.g., a dye signature). Various assay formats for detection of *Borrelia* specific antibodies are illustrated in FIGS. 1-3 and, as discussed above, Osp C type B and/or Osp C type I can be substituted by any of the other Osp C protein types discussed above (e.g., types A, C-H and J-U).

As discussed above, the disclosed *Borrelia* specific peptides and proteins can be immobilized on a substrate. Thus, the subject application also pertains to novel combinations of *Borrelia* specific peptides and proteins immobilized on a substrate. As discussed above, Osp C type B and/or Osp C type I can be substituted by any of the other Osp C protein types discussed above (e.g., types A, C-H and J-U). Accordingly, the peptides and proteins can be immobilized on a substrate a singly or in various combinations as set forth in the Substrate/Antigen Combination tables disclosed herein. By way of example, designated pFlaB-mV can be immobilized on a first particle having a first specific detectable physical parameter (e.g., dye signature), pErp59-mV can be immobilized on a second particle having a second specific detectable physical parameter (e.g., dye signature), pP35-mV can be immobilized on a third particle having a third specific detectable physical parameter (e.g., dye signature), p58 can be immobilized on a fourth particle having a fourth specific detectable physical parameter (e.g., dye signature), outer surface protein C (Osp C) type B can be immobilized on a fifth particle having a fifth specific detectable physical parameter (e.g., dye signature), outer surface protein C (Osp C) type I can be immobilized on an sixth particle having a sixth specific detectable physical parameter (e.g., dye signature), and DbpA can be immobilized on a seventh particle having a seventh specific detectable physical parameter (e.g., dye signature). In this non-limiting example, each of the seven substrates have a distinct specific detectable physical parameter (e.g., a dye signature) that permits for the differentiation of each substrate on which a *Borrelia* specific peptide or protein has been immobilized. Likewise, substrates having a specific detectable physical parameter (e.g., dye signature) can be used to immobilize a particular combination of *Borrelia* specific peptides and/or proteins such that that each particular combination of *Borrelia* specific peptides and/or proteins can be distinguished from a different particular combination of *Borrelia* specific peptides and/or proteins on the basis of its specific detectable physical parameter (e.g., dye signature). Alternatively, various antigen combinations can be immobilized on a single substrate, e.g., an ELISA well, dipstick, microtiter plate, flow-through assay device, chips, microchips, lateral flow devices or an immunocapillary or immunochromatographic immunoassay device). Various antigen combinations are set forth in the Substrate/Antigen Combination tables disclosed herein.

In certain embodiments, the following peptides and/or proteins, as well as various combinations thereof, can used for detecting *Borrelia* specific antibodies in a biological sample. Thus, each peptide and/or protein analyte can be immobilized on a substrate (e.g., bead) having a specific detectable parameter giving rise to a detection assay providing distinct/unique detectable parameters. As discussed above, Osp C type B and/or Osp C type I can be substituted by any of the other Osp C protein types discussed above (e.g., types A, C-H and J-U). For example, each peptide or protein can be used individually for the detection of *Borrelia* specific antibodies in a biological sample. In other examples, combinations of peptides and/or proteins can be used. Accordingly, a peptide and/or protein combination that comprises: a) a first peptide selected from pFlaB-mV; pErp59-mV; pP35-mV and combinations thereof; and, optionally, b) a proteins selected from OspC-type B; OspC-type I; DbpA; p58 and combinations thereof can be bound to a substrate to detect *Borrelia* specific antibodies in a biological sample.

Non-limiting examples of various combinations include: pFlaB-mV alone; pErp59-mV alone; pP35-mV alone;

pFlaB-mV in combination with pErp59-mV; pFlaB-mV in combination with pP35-mV; pErp59-mV in combination with pP35-mV; and pFlaB-mV, pErp59-mV and pP35-mV. Each of these combinations from the first set of *Borrelia* antigens can be utilized in the disclosed immunoassays alone or in combination with a second set of *Borrelia* antigens selected from OspC-type B, OspC-type I, DbpA, p58, or any combination thereof. Thus, pErp59-mV can be used in combination with one or more protein selected from OspC-type B, OspC-type I, DbpA and p58; pP35-mV can be used in combination with one or more protein selected from OspC-type B, OspC-type I, DbpA and p58; pFlaB-mV can be used in combination with one or more protein selected from OspC-type B, OspC-type I, DbpA and p58; pFlaB-mV in combination with pErp59-mV can be used in combination with one or more protein selected from OspC-type B, OspC-type I, DbpA and p58; pFlaB-mV in combination with pP35-mV can be used in combination with one or more protein selected from OspC-type B, OspC-type I, DbpA and p58; pErp59-mV in combination with pP35-mV can be used in combination with one or more protein selected from OspC-type B, OspC-type I, DbpA and p58; and pFlaB-mV, pErp59-mV and pP35-mV can be used in combination with one or more protein selected from OspC-type B, OspC-type I, DbpA and p58. Non-limiting examples of the combinations of OspC-type B, OspC-type I, DbpA and p58 include: OspC-type B and OspC-type I; OspC-type B and DbpA; OspC-type B and p58; OspC-type I and DbpA; OspC-type I and p58; DbpA and p58; OspC-type B, OspC-type I and DbpA; OspC-type B, OspC-type I and p58; OspC-type B, DbpA and p58; OspC-type I, DbpA and p58; and OspC-type B, OspC-type I, DbpA and p58. As discussed above, Osp C type B and/or Osp C type I can be substituted by any of the other Osp C protein types discussed above (e.g., types A, C-H and J-U).

| Two Substrate/Antigen Combinations | |
|---|---|
| A and B | C and D |
| A and C | C and E |
| A and D | C and F |
| A and E | C and G |
| A and F | D and E |
| A and G | D and F |
| B and C | D and G |
| B and D | E and F |
| B and E | E and G |
| B and F | F and G |
| B and G | |

| Three Substrate/Antigen Combinations | |
|---|---|
| A and B and C | B and C and G |
| A and B and D | B and D and E |
| A and B and E | B and D and F |
| A and B and F | B and D and G |
| A and B and G | B and E and F |
| A and C and D | B and E and G |
| A and C and E | B and F and G |
| A and C and F | C and D and E |
| A and C and G | C and D and F |
| A and D and E | C and D and G |
| A and D and F | C and E and F |
| A and D and G | C and E and G |
| A and E and F | C and F and G |
| A and E and G | D and E and F |
| A and F and G | D and E and G |
| B and C and D | D and F and G |
| B and C and E | E and F and G |
| B and C and F | |

| Four Substrate/Antigen Combinations | |
|---|---|
| A and B and C and D | A and E and F and G |
| A and B and C and E | B and C and D and E |
| A and B and C and F | B and C and D and F |
| A and B and C and G | B and C and D and G |
| A and B and D and E | B and C and E and F |
| A and B and D and F | B and C and E and G |
| A and B and D and G | B and C and F and G |
| A and B and E and F | B and D and E and F |
| A and B and E and G | B and D and E and G |
| A and B and F and G | B and D and F and G |
| A and C and D and E | B and E and F and G |
| A and C and D and F | C and D and E and F |
| A and C and D and G | C and D and E and G |
| A and C and E and F | C and D and F and G |
| A and C and E and G | C and E and F and G |
| A and C and F and G | D and E and F and G |
| A and D and E and F | |
| A and D and E and G | |
| A and D and F and G | |

| Five Substrate/Antigen Combinations | |
|---|---|
| A and B and C and D and E | A and C and D and E and G |
| A and B and C and D and F | A and C and D and F and G |
| A and B and C and D and G | A and C and E and F and G |
| A and B and C and E and F | A and D and E and F and G |
| A and B and C and E and G | B and C and D and E and F |
| A and B and C and F and G | B and C and D and E and G |
| A and B and D and E and F | B and C and D and F and G |
| A and B and D and E and G | B and C and E and F and G |
| A and B and D and F and G | B and D and E and F and G |
| A and B and E and F and G | C and D and E and F and G |
| A and C and D and E and F | |

| Six Substrate/Antigen Combinations |
|---|
| A and B and C and D and E and F |
| A and B and C and D and E and G |
| A and B and C and D and F and G |
| A and B and C and E and F and G |
| A and B and D and E and F and G |
| A and C and D and E and F and G |
| B and C and D and E and F and G |

| Seven Substrate/Antigen Combination |
|---|
| A and B and C and D and E and F and G |

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Coupling/Immobilization of Peptide and Recombinant Protein Antigens The protein and peptide antigens (e.g., pFlaB-mV, pErp59-mV, pP35-mV, OspC-types I and B, DbpA, P58 or combinations thereof) were immobilized on a solid support (e.g., microparticles, beads, or surface such as a chip, microliter plate, membrane, or glass). In some immobilization protocols, carboxylated beads were activated and esterified before adding *Borrelia* specific peptide and protein antigen(s). Carboxyl activation was achieved using a water soluble carbodiimide, such as 1-cyclohexyl-3-(2-morpholinoethyl) carbodiimide (CMC). Esterification was achieved using NHS, NHSS or HOBt. After the carboxyl activation and esterification, the *Borrelia* protein and peptide antigen(s) were added to the actived surface in buffers with pH between 6-10. For example sodium acetate buffer pH 5.1, phosphate buffer pH 7.0 with or without detergent (e.g., CHAPS, ionic and zwitterionic detergents). After coupling/immobilization, the solid support was blocked in buffers containing protein blocker (such as BSA, mouse IgG, bovine gamma globulin (BGG), animal serum (goat, horse, murine)). The protein blocker(s) were present in amounts ranging from 0.1-10 weight/volume percent.

Example 2—Detection of *Borrelia* Antibodies

Once the solid support was coated with peptide and protein antigens either individually or in different combinations as described above, the coated solid support(s) was contacted with the sample, e.g., a biological sample from an individual suspected of having been exposed to Lyme disease. Unbound sample was washed away and labeled anti-Ig antibodies were added to allow for detection of antibodies from the sample bound to the solid support. Where the sample was from a human, labeled anti-human Ig antibodies were used. For example, a mixture of anti-human IgG and anti-human IgM antibodies, or an antibody that binds both IgG and IgM, were used (FIG. 1).

The performance (specificity and sensitivity) of peptides and proteins tested either individually or in combination against EIA using the BIOPLEX 2200 Lyme total assay test are provided in Table 1. Normal and diseased samples were collected from endemic and non-endemic regions of the United States. Samples were considered positive if any one of the analytes (peptide and/or protein) tested positive by the BioPlex assay. Improved sensitivity was achieved when peptide and protein coated solid surface (e.g., beads) was tested together as compared to either peptide or protein coated surface alone (Table 1).

Example 3—Comparison of the Disclosed Multiplex Assay Against EIA and 2-Tier Testing Algorithms This example illustrates the performance of the disclosed multiplex *Borrelia* total assay against EIA and 2-tier testing algorithm on one set of clinically characterized serum samples from CDC with known disease stages (Panel A; N=32). Patient samples were tested for the presence of Lyme total (IgG and IgM) antibodies using the BIOPLEX 2200 platform. Readings were obtained by a flow cytometer that detects each bead region according to its fluorescent dye signature, as well as the presence of antibodies bound to each bead. Essentially, each sample is incubated with the bead reagent to allow disease specific antibodies to bind antigen coated beads. The unbound sample components are aspirated, and coupled beads are washed. In the second step, washed beads are incubated with the conjugate reagent containing anti-human IgG-PE and IgM-PE. After a short incubation period, excess conjugate reagent is removed and beads washed. Subsequently, washed beads are suspended in sheath fluid and sent to the detector.

TABLE 2

Performance of the multiplex Lyme total assay against clinically characterized samples.

| | Panel A N = 32 | |
|---|---|---|
| Assay Type | Clinical Sensitivity | Clinical Specificity |
| EIA | 66.60% | 80.00% |
| 2-tier | 66.60% | 100.00% |
| BIOPLEX 2200 | 83.30% | 90.00% |

Lyme specific signals associated with each bead were compared to matched calibrators and results reported. A comparison of results obtained from Lyme total test and those from comparators are listed in Table 2. The Lyme total assay detected antibodies in 10 of 12 disease samples (clinical sensitivity 83.3%) including two positive patient samples

TABLE 1

Schematic illustration of a Lyme total assay for the detection of *Borrelia* specific antibodies on an automated platform (BIOPLEX 2200).

| Performance | Sample Cohort | pFlaB-mV | pErP59-mV | pFlaB-mV + pErp59-mV | pFlaB-mV + OspC-I | pFlaB-mV + OspC-B | pErp59-mV + OspC-I | pErp59-mV + OspC-B | pFlaB-mV + pErp59-mV + OspC-I | pFlaB-mV + pErp59-mV + OspC-B | All markers |
|---|---|---|---|---|---|---|---|---|---|---|---|
| Specificity (Negative Test Results) | Normal (Endemic Region) | 99% | 99% | 98% | 97% | 97% | 97% | 97% | 97% | 97% | 97% |
| | Normal (Non-endemic Region) | 98% | 98% | 98% | 97% | 97% | 97% | 97% | 97% | 97% | 97% |
| | All Normals | 99% | 99% | 99% | 98% | 98% | 98% | 98% | 97% | 97% | 97% |
| Sensitivity (Positive Test Results) | Lyme (IgG Positives) | 96% | 96% | 97% | 97% | 97% | 97% | 97% | 97% | 97% | 97% |
| | Lyme (IgM positives) | 61% | 63% | 64% | 73% | 71% | 75% | 74% | 75% | 74% | 75% |
| | All Diseased Samples | 53% | 56% | 56% | 61% | 60% | 63% | 62% | 63% | 62% | 63% | collected at five days post-symptom onset (Erythema migrans). Both these samples were missed by EIA and the 2-tier testing algorithm (Table 3). The multiplex total assay also identified 18 of 20 negatives (12 disease controls and 8 healthy controls) as negatives (clinical specificity 90%).

The performance of the disclosed multiplex immunoassay testing for the presence of IgM antibodies was also compared to the European test using the sample cohort discussed above without CSF samples (Table 5). Compared to 5% (10/200) Lyme IgM prevalence among blood bank samples,

TABLE 3

Detection of anti-*Borrelia* antibodies among clinically characterized patient samples from all three disease stages.

| Sample ID | Bio-Rad Results | Sample Category | Sample Group | Acute/ Convalescent | EIA Interpretation | IgM WB Interpretation | IgG WB Interpretation | 2-Tier Interpretation | C6 ELISA |
|---|---|---|---|---|---|---|---|---|---|
| 0001 | Negative | Lyme disease | Early Lyme-EM | Acute | Neg | Neg | Neg | Neg | Neg |
| 0002 | Negative | Lyme disease | Early Lyme-EM | Acute | Neg | Neg | Neg | Neg | Neg |
| 0003 | Positive | Lyme disease | Early Lyme-EM | Acute | Neg | Neg | Neg | Neg | Neg |
| 0004 | Positive | Lyme disease | Early Lyme-EM | Acute | Neg | Pos | Neg | Neg | Neg |
| 0005 | Positive | Lyme disease | Early Lyme-EM | Convalescent | Pos | Pos | Neg | Pos | Pos |
| 0006 | Positive | Lyme disease | Early Lyme-EM | Convalescent | Pos | Pos | Neg | Pos | Pos |
| 0007 | Positive | Lyme disease | Early Lyme-EM | Convalescent | Pos | Pos | Pos | Pos | Pos |
| 0008 | Positive | Lyme disease | Early Lyme-EM | Convalescent | Pos | Pos | Neg | Pos | Pos |
| 0009 | Positive | Lyme disease | Neurologic Lyme | — | Pos | Pos | Pos | Pos | Pos |
| 0010 | Positive | Lyme disease | Neurologic Lyme | — | Pos | Pos | Pos | Pos | Pos |
| 0011 | Positive | Lyme disease | Lyme arthritis | — | Pos | Neg | Pos | Pos | Pos |
| 0012 | Positive | Lyme disease | Lyme arthritis | — | Pos | Neg | Pos | Pos | Pos |

Example 4—Comparison of the Disclosed Multiplex Assay Against the PROGEN *Borrelia* Indirect Immunofluorescence Test In this example, the performance of the disclosed multiplex immunoassay for the detection of Lyme disease IgG antibodies was compared to the results from a test developed in Europe. The European test uses a modified PROGEN *Borrelia* IF immunoassay system with antigen supplied by Mikrogen Diagnostics (PROGEN Biotechnik GmbH, Heidelberg, Germany). The test used 200 normal blood bank samples, 100 test ordered samples and 300 Lyme positive (IgG and/or IgM) for a total of 600 serum samples and 50 matched serum-CSF samples (Table 4). Compared to 16% (32/200) prevalence among blood bank samples using the modified PROGEN immunoassay, the disclosed multiplex immunoassay revealed a prevalence of 6% (6/100). For the Lyme positive sample cohort, a positive agreement of 93.3% (280/300) was observed between the disclosed multiplex immunoassay testing for IgG test results and the corresponding IgG and IgM predicate results developed using the modified PROGEN immunoassay. Under similar assay conditions, 80% (8/10) of CSF samples tested Lyme IgG positive with a negative agreement of 87.5% (35/40).

TABLE 4

Performance of Lyme IgG assay using blood bank normals, test ordered normal, Lyme IgG and IgM positive and diseased and non-diseased CSF samples from Europe.

| Sample Cohort | N | Postive Agreement[1] (%) | Negative Agreement[1] (%) |
|---|---|---|---|
| Blood Bank Normals | 200 | 32 (16%) | 168 (84%) |
| Test Ordered Normals | 100 | 6 (6%) | 94 (94%) |
| Lyme Positives | 300 | 280 (93.3%) | 20 (6.7%) |
| CSF Lyme Positive | 10 | 8 (80%) | 2 (20%) |
| CSF Lyme Negative | 40 | 5 (12.5%) | 35 (87.5%) | the disclosed multiplex immunoassay revealed a prevalence of 2% (2/100). For the Lyme positive samples, a positive agreement of 58% (174/300) was observed between the multiplex IgM test results and the corresponding predicate results from the European test.

TABLE 5

Performance of Lyme IgM assay using blood bank normal, test ordered normal, Lyme positive European samples.

| Sample Cohort | N | Postive Agreement[1] (%) | Negative Agreement[1] (%) |
|---|---|---|---|
| Blood Bank Normals | 200 | 10 (5%) | 190 (95%) |
| Test Ordered Normals | 100 | 2 (2%) | 98 (98%) |
| Lyme Positives | 300 | 174 (58%) | 126 (42%) |

The performance of the disclosed *Borrelia* assay using a subset from Table 4 of 280 predicate negative and 216 IgG predicate positive samples from Europe is provided in Table 6 with data analyzed for multiple peptide and protein combinations. Samples were considered positive if any one of the analytes (peptides and/or proteins) generated positive results (e.g., specific antibody binding to the analyte was detected using labeled anti-human Ig antibodies). Once again, improved sensitivity was achieved when certain peptide and protein coated beads were included in the assay together due to the antigen and *Borrelia* species variation seen in Europe.

TABLE 6

Additional analysis of European Lyme samples using anti-human anti-IgG labeled antibodies.

|  | Peptides | Peptides + p100 | Peptides + p41 | Peptides + OspC-type E | Peptides + DbpA | Peptides + BmpA | Peptides + P58 | Peptides + DbpA + P58 |
|---|---|---|---|---|---|---|---|---|
| Specificity | 99.6% | 99.3% | 97.1% | 98.9% | 98.6% | 99.6% | 98.2% | 97.5% |
| Specificity | 83.8% | 84.8% | 83.8% | 84.3% | 93.5% | 84.3% | 90.7% | 95.8% |

280 predicate negative samples
216 predicate positive samples
Cohort: Blood bank negative, test ordered, IgG only predicate positive, IgG + IgM predicate positive
Detection with anti-human IgG
"Peptides" = pFlaB-mV, pErp59-mV and pP35-mV

REFERENCES

1. Aguero-Rosenfeld M E, Wang G, Schwartz I, Wormser G P. Diagnosis of Lyme Borreliosis. Clin. Micrbiol. Rev. 18:484-509, 2005.
2. Stanek G, Wormser G P, Gray J, Strle F. *Lyme borreliosis*. Lancet 379:461-473, 2012.
3. Fikrig E, Berland R, Chen M, Williams S, Signal L H, and Flavell R A. Serological response to *B. burgdorferi* Flagellin demonstrates an epitope common to a neuroblastoma cell line. Proc. Natl. Acad. Sci. 90:183-187, 1993.
4. Centers for Disease Control and Prevention. Recommendations for test performance and interpretation from the second national conference on serologic diagnosis of Lyme disease. Morb. Mortal. Wkly Rep. 44:590-591, 1995.
5. Molins C R, Sexton C, Young J W, Ashton L V, Pappert R, Beard C B, Schriefer M E. Collection and characterization of samples for establishment of a serum repository for Lyme disease diagnostic test development and evaluation. J Clin Microbiol. 52:3755-3762, 2014.
6. Brouqui P, Bacellar F, Baranton G, Birtles R J, Bjoërsdorff A, Blanco J R, Caruso G, Cinco M, Fournier P E, Francavilla E, Jensenius M, Kazar J, Laferl H, Lakos A, Lotric Furlan S, Maurin M, Oteo J A, Parola P, Perez-Eid C, Peter O, Postic D, Raoult D, Tellez A, Tselentis Y, Wilske B. ESCMID Study Group on *Coxiella, Anaplasma, Rickettsia* and *Bartonella*. European Network for Surveillance of Tick-Borne Diseases. Guidelines for the diagnosis of tick-borne bacterial diseases in Europe. Clin. Microbiol. Infect. 10:1108-1132, 2004.
7. Branda J A, Aguero-Rosenfeld M E, Ferraro M J, Johnson B J, Wormser G P, Steere A C. 2-tiered antibody testing for early and late Lyme disease using only an immunoglobulin G blot with the addition of a VlsE band as the second-tier test. Clin. Infect. Dis. 50:20-26, 2010.
8. Bacon R M, Biggerstaff B J, Schriefer M E, Gilmore R D, Philipp M T, Steere A C, Wormser G P, Marques A R, Johnson B J. Serodiagnosis of Lyme disease by kinetic enzyme-linked immunosorbent assay using recombinant VlsE1 or peptide antigens of *Borrelia burgdorferi* compared with 2-tiered testing using whole-cell lysates. J. Infect. Dis. 187:1187-1199, 2003.
9. Dattwyler R J, Gomez-Solecki M. Peptide diagnostic agent for Lyme disease. U.S. Pat. No. 7,887,815 dated Feb. 15, 2011.
10. Dattwyler R J, Arnaboldi P M. Diagnostic peptides for Lyme disease. US Patent Application 20150017666 dated Jan. 15, 2015.
11. Dattwyler R J, Gomez-Solecki M J C, Luft, B J, Dunn J J. Recombinant constructs of *Borrelia burgdorferi*. U.S. Pat. No. 7,008,625 dated Mar. 7, 2006.
12. Dattwyler R J, Seinost G, Dykhuizen D, Luft, B J, Gomez-Solecki M J C. Groups of *Borrelia burgdorferi* and *Borrelia afzalii* that cause Lyme disease in humans. U.S. Pat. No. 7,582,304B2 dated Sep. 1, 2009.

We claim:

1. A substrate comprising SEQ ID NO: 2, SEQ ID NO: 8 and SEQ ID NO: 7 each immobilized on said substrate.

2. The substrate according to claim 1, wherein said substrate is glass, plastic, polystyrene or nitrocellulose.

3. The substrate according to claim 1, wherein said substrate is a particle, a bead, a chip, a microchip, a lateral flow substrate or a microtiter plate.

4. The substrate according to claim 3, wherein said substrate is a population of particles or beads.

5. The substrate of claim 4, wherein said population of particles or beads comprises three or more separate subpopulations of particles or beads, each subpopulation of particles or beads being distinguishable by a specific detectable physical parameter, SEQ ID NO: 2 being immobilized on one subpopulation of particles or beads, SEQ ID NO: 8 being immobilized on a second subpopulation of particles or beads, and SEQ ID NO: 7 being immobilized on a third subpopulation of particles or beads.

6. The substrate of claim 5, wherein each of the three or more separate subpopulations of particles or beads has a separate specific detectable physical parameter.

7. The substrate of claim 6, wherein the specific detectable physical parameter is a fluorescent dye, a fluorophore, a luminescent agent, an electron-dense reagent, a radioisotope, or a particle size.

8. The substrate of claim 7, wherein the specific detectable physical parameter is a fluorophore.

9. A method of detecting antibodies specific to SEQ ID NO: 2, SEQ ID NO: 8 and/or SEQ ID NO: 7 in a mammal comprising obtaining a biological sample from the mammal, contacting said biological sample with the substrate of claim 1 and detecting the presence or the absence of the antibodies that are bound specifically to SEQ ID NO: 2, SEQ ID NO: 8 and/or SEQ ID NO: 7.

10. The method of claim 9, wherein the specific detectable parameter is a fluorescent dye, a fluorophore, a luminescent agent, an electron-dense reagent, a radioisotope, or a particle size.

11. The method of claim 10, wherein the specific detectable physical parameter is a fluorophore.

* * * * *

SEQUENCE LISTING

<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Polyhistidine-tag

<400> SEQUENCE: 1

His His His His His His
1               5

<210> SEQ ID NO 2
<211> LENGTH: 34
<212> TYPE: PRT
<213> ORGANISM: Artificial Sequence
<220> FEATURE:

```
<223> OTHER INFORMATION: synthetic fusion peptide

<400> SEQUENCE: 2

Cys Val Gln Glu Gly Val Gln Gln Glu Gly Ala Gln Gln Pro Gly Gly
1               5                   10                  15

Gly Met Lys Lys Asn Asp Gln Ile Val Ala Ala Ile Ala Leu Arg Gly
            20                  25                  30

Val Ala

<210> SEQ ID NO 3
<211> LENGTH: 35
<212> TYPE: PRT
<213> ORGANISM: Artificial Sequence
<220> FEATURE:
<223> OTHER INFORMATION: synthetic fusion peptide

<400> SEQUENCE: 3

Lys Ile Glu Phe Ser Lys Phe Thr Val Lys Ile Lys Asn Lys Asp Gly
1               5                   10                  15

Gly Gly Met Lys Lys Asn Asp Gln Ile Val Ala Ala Ile Ala Leu Arg
            20                  25                  30

Gly Val Ala
        35

<210> SEQ ID NO 4
<211> LENGTH: 35
<212> TYPE: PRT
<213> ORGANISM: Artificial Sequence
<220> FEATURE:
<223> OTHER INFORMATION: synthetic fusion peptide

<400> SEQUENCE: 4

Asp Thr Gly Ser Glu Arg Ser Ile Arg Tyr Arg Arg Val Tyr Gly
1               5                   10                  15

Gly Gly Met Lys Lys Asn Asp Gln Ile Val Ala Ala Ile Ala Leu Arg
            20                  25                  30

Gly Val Ala
        35

<210> SEQ ID NO 5
<211> LENGTH: 193
<212> TYPE: PRT
<213> ORGANISM: Borrelia burgdorferi

<400> SEQUENCE: 5

Met Thr Leu Phe Leu Phe Ile Ser Cys Asn Asn Ser Gly Lys Asp Gly
1               5                   10                  15

Asn Thr Ser Ala Asn Ser Ala Asp Glu Ser Val Lys Gly Pro Asn Leu
            20                  25                  30

Thr Glu Ile Ser Lys Lys Ile Thr Asp Ser Asn Ala Val Leu Leu Ala
        35                  40                  45

Val Lys Glu Val Glu Ala Leu Leu Ser Ser Ile Asp Glu Leu Ala Lys
    50                  55                  60

Ala Ile Gly Lys Lys Ile Lys Asn Asp Gly Ser Leu Asp Asn Glu Ala
65                  70                  75                  80

Asn Arg Asn Glu Ser Leu Leu Ala Gly Ala Tyr Thr Ile Ser Thr Leu
                85                  90                  95

Ile Thr Gln Lys Leu Ser Lys Leu Asn Gly Ser Glu Gly Leu Lys Glu
            100                 105                 110
```

```
Lys Ile Ala Ala Ala Lys Lys Cys Ser Glu Glu Phe Ser Thr Lys Leu
            115                 120                 125

Lys Asp Asn His Ala Gln Leu Gly Ile Gln Gly Val Thr Asp Glu Asn
            130                 135                 140

Ala Lys Lys Ala Ile Leu Lys Ala Asn Ala Ala Gly Lys Asp Lys Gly
145                 150                 155                 160

Val Glu Glu Leu Glu Lys Leu Ser Ser Leu Glu Ser Leu Ser Lys Ala
                165                 170                 175

Ala Lys Glu Met Leu Ala Asn Ser Val Lys Glu Leu Thr Ser Pro Val
            180                 185                 190

Val

<210> SEQ ID NO 6
<211> LENGTH: 191
<212> TYPE: PRT
<213> ORGANISM: Borrelia burgdorferi

<400> SEQUENCE: 6

Met Thr Leu Phe Leu Phe Ile Ser Cys Asn Asn Ser Gly Lys Asp Gly
1               5                   10                  15

Asn Thr Ser Ala Asn Ser Ala Asp Glu Ser Val Lys Gly Pro Asn Leu
            20                  25                  30

Thr Glu Ile Ser Lys Lys Ile Thr Glu Ser Asn Ala Val Val Leu Ala
        35                  40                  45

Val Lys Glu Val Glu Thr Leu Leu Thr Ser Ile Asp Glu Leu Ala Lys
50                  55                  60

Ala Ile Gly Lys Lys Ile Lys Asn Asp Val Ser Leu Asp Asn Glu Ala
65                  70                  75                  80

Asp His Asn Gly Ser Leu Ile Ser Gly Ala Tyr Leu Ile Ser Asn Leu
                85                  90                  95

Ile Thr Lys Lys Ile Ser Ala Ile Lys Asp Ser Gly Glu Leu Lys Ala
            100                 105                 110

Glu Ile Glu Lys Ala Lys Lys Cys Ser Glu Glu Phe Thr Ala Lys Leu
            115                 120                 125

Lys Gly Glu His Thr Asp Leu Gly Lys Glu Gly Val Thr Asp Asp Asn
            130                 135                 140

Ala Lys Lys Ala Ile Leu Lys Thr Asn Asn Asp Lys Thr Lys Gly Ala
145                 150                 155                 160

Asp Glu Leu Glu Lys Leu Phe Glu Ser Val Lys Asn Leu Ser Lys Ala
                165                 170                 175

Ala Lys Glu Met Leu Thr Asn Ser Val Lys Glu Leu Thr Ser Pro
            180                 185                 190

<210> SEQ ID NO 7
<211> LENGTH: 170
<212> TYPE: PRT
<213> ORGANISM: Borrelia afzelii

<400> SEQUENCE: 7

Met Ile Lys Tyr Asn Lys Ile Ile Leu Thr Leu Thr Leu Leu Ala Ser
1               5                   10                  15

Leu Leu Ala Ala Cys Ser Leu Thr Gly Lys Ala Arg Leu Glu Ser Ser
            20                  25                  30

Val Lys Asp Ile Thr Asn Glu Ile Glu Lys Ala Ile Lys Glu Ala Glu
        35                  40                  45

Asp Ala Gly Val Lys Thr Asp Ala Phe Thr Glu Thr Gln Thr Gly Gly
```

```
            50                  55                  60
Lys Val Ala Gly Pro Lys Ile Arg Ala Ala Lys Ile Arg Val Ala Asp
 65                  70                  75                  80

Leu Thr Ile Lys Phe Leu Glu Ala Thr Glu Glu Thr Ile Thr Phe
                     85                  90                  95

Lys Glu Asn Gly Ala Gly Asp Glu Phe Ser Gly Ile Tyr Asp Leu
                    100                 105                 110

Ile Leu Asn Ala Ala Lys Ala Val Glu Lys Ile Gly Met Lys Asp Met
                    115                 120                 125

Thr Lys Thr Val Glu Glu Ala Ala Lys Glu Asn Pro Lys Thr Thr Ala
                    130                 135                 140

Asn Gly Ile Ile Glu Ile Val Lys Val Met Lys Ala Lys Val Glu Asn
145                 150                 155                 160

Ile Lys Glu Lys Gln Thr Lys Asn Gln Lys
                    165                 170

<210> SEQ ID NO 8
<211> LENGTH: 527
<212> TYPE: PRT
<213> ORGANISM: Borrelia garinii

<400> SEQUENCE: 8

Met Lys Leu Gln Lys Leu Leu Phe Ser Val Ile Phe Phe Leu Thr Phe
  1               5                  10                  15

Leu Cys Cys Asn Lys Glu Glu Lys Glu Gly Ile Ser Phe Lys Ile
                 20                  25                  30

Ser Leu Gly Ser Glu Pro Ser Leu Asp Pro Gln Leu Ala Asp Asp
             35                  40                  45

Asn Val Gly Ser Lys Met Ile Asp Thr Met Phe Arg Gly Leu Ile Thr
 50                  55                  60

Gly Asp Pro Asn Thr Gly Asn Lys Pro Gly Leu Ala Lys Ser Trp
 65                  70                  75                  80

Asp Ile Ser Pro Asp Gly Thr Val Tyr Thr Phe Thr Leu Arg Glu Lys
                 85                  90                  95

Ile Ile Trp Ser Asp Gly Val Ala Ile Thr Ala Glu Gly Ile Arg Lys
                100                 105                 110

Ser Tyr Leu Arg Ile Leu Asn Lys Glu Thr Gly Ser Asn Tyr Ala Glu
                115                 120                 125

Met Val Lys Ser Thr Ile Lys Asn Gly Gln Lys Tyr Phe Asp Gly Gln
                130                 135                 140

Val Ser Asp Ser Glu Leu Gly Ile Arg Ala Ile Asp Glu Lys Thr Leu
145                 150                 155                 160

Glu Ile Thr Leu Glu Ser Pro Lys Pro Tyr Phe Ile Asp Met Leu Val
                165                 170                 175

His Gln Ser Phe Ile Pro Ile Pro Ile His Ile Ala Glu Lys Tyr Gly
                180                 185                 190

Gln Ser Trp Thr Ser Pro Glu Asn Ile Val Thr Ser Gly Pro Phe Lys
                195                 200                 205

Leu Lys Glu Arg Ile Pro Asn Glu Lys Tyr Val Val Glu Lys Asn Asp
                210                 215                 220

Lys Tyr Tyr Asn Ser Asn Gln Val Glu Val Gln Glu Ile Thr Phe Tyr
225                 230                 235                 240

Thr Thr Asn Asp Ser Ser Thr Ala Tyr Lys Met Tyr Glu Asn Lys Glu
                245                 250                 255
```

-continued

```
Leu Asp Ala Ile Phe Gly Ser Ile Pro Pro Asp Leu Ile Lys Asp Leu
            260                 265                 270

Lys Leu Arg Ser Asp Tyr Tyr Ser Ala Val Asn Ala Ile Tyr Phe
        275                 280                 285

Tyr Ala Phe Asn Thr Tyr Ile Lys Pro Leu Asp Asn Val Lys Val Arg
    290                 295                 300

Lys Ala Leu Thr Leu Ala Ile Asp Arg Glu Thr Leu Thr Tyr Lys Val
305                 310                 315                 320

Leu Asp Asn Gly Thr Thr Pro Thr Arg Arg Ile Ala Pro Asn Phe Ser
                325                 330                 335

Ser Tyr Ser Tyr Ala Lys Asn Leu Glu Leu Phe Asn Pro Glu Ile Ala
            340                 345                 350

Lys Thr Leu Leu Ala Glu Ala Gly Tyr Pro Asn Gly Asn Gly Phe Pro
        355                 360                 365

Ile Leu Lys Leu Lys Tyr Asn Thr Ser Glu Ala His Lys Lys Ile Cys
    370                 375                 380

Glu Phe Ile Gln Asn Gln Trp Lys Lys Ile Leu Asn Ile Asp Val Glu
385                 390                 395                 400

Leu Glu Asn Glu Glu Trp Thr Thr Tyr Leu Asn Thr Arg Ser Asn Gly
                405                 410                 415

Asn Tyr Glu Ile Ala Arg Ala Gly Trp Ile Gly Asp Tyr Ala Asp Pro
            420                 425                 430

Leu Thr Phe Leu Ser Ile Phe Thr Gln Gly Tyr Thr Gln Phe Ser Ser
        435                 440                 445

His Asn Tyr Ser Ser Pro Glu Tyr Asn Glu Leu Ile Lys Lys Ser Asp
    450                 455                 460

Leu Glu Leu Asp Pro Ile Lys Arg Gln Asp Ile Leu Arg Lys Ala Glu
465                 470                 475                 480

Glu Ile Ile Ile Glu Lys Asp Phe Pro Ile Ala Pro Ile Tyr Ile Tyr
                485                 490                 495

Gly Asn Ser Tyr Leu Phe Arg Asn Asp Lys Trp Thr Gly Trp Asn Thr
            500                 505                 510

Asn Ile Thr Glu Arg Phe Asp Leu Ser Gln Leu Lys Leu Lys Asn
        515                 520                 525

<210> SEQ ID NO 9
<211> LENGTH: 6
<212> TYPE: PRT
<213> ORGANISM: Artificial Sequence
<220> FEATURE:
<223> OTHER INFORMATION: linker

<400> SEQUENCE: 9

Gly Gly Ser Gly Ser Gly
1               5

<210> SEQ ID NO 10
<211> LENGTH: 18
<212> TYPE: PRT
<213> ORGANISM: Artificial Sequence
<220> FEATURE:
<223> OTHER INFORMATION: linker

<400> SEQUENCE: 10

Gly Ser Thr Ser Gly Ser Gly Lys Pro Gly Ser Gly Glu Gly Ser Thr
1               5                   10                  15

Lys Gly
```

```
<210> SEQ ID NO 11
<211> LENGTH: 7
<212> TYPE: PRT
<213> ORGANISM: Artificial Sequence
<220> FEATURE:
<223> OTHER INFORMATION: linker

<400> SEQUENCE: 11

Ser Gly Arg Ala His Ala Gly
1               5

<210> SEQ ID NO 12
<211> LENGTH: 4
<212> TYPE: PRT
<213> ORGANISM: Artificial Sequence
<220> FEATURE:
<223> OTHER INFORMATION: linker

<400> SEQUENCE: 12

Gly Ser Ser Gly
1
```